US005679840A

United States Patent [19]
Knöfel et al.

[11] Patent Number: 5,679,840
[45] Date of Patent: Oct. 21, 1997

[54] FRACTIONATION AND PURIFICATION OF AROMATIC POLYAMINE MIXTURES AND THE USE THEREOF

[75] Inventors: Hartmut Knöfel, Odenthal; Michael Brockelt, Leverkusen, both of Germany

[73] Assignee: Bayer Aktiengesellschaft, Leverkusen, Germany

[21] Appl. No.: 623,240

[22] Filed: Mar. 28, 1996

[30] Foreign Application Priority Data

Apr. 7, 1995 [DE] Germany .................. 195 13 146.0

[51] Int. Cl.[6] ............................................. C07C 209/86
[52] U.S. Cl. ................... 560/347; 564/315; 564/331; 564/332; 564/333; 564/334; 564/437; 564/450; 564/451
[58] Field of Search ........................ 564/315, 331, 564/332, 333, 334, 437, 450, 451; 560/347

[56] References Cited

U.S. PATENT DOCUMENTS

| 4,087,459 | 5/1978 | Knöfel et al. | 564/331 |
| 4,914,236 | 4/1990 | Knöfel et al. | 564/334 |
| 4,924,028 | 5/1990 | Knofel et al. | 564/331 |
| 5,196,591 | 3/1993 | Knofel et al. | 564/331 |
| 5,359,141 | 10/1994 | Knofel et al. | 564/331 |

FOREIGN PATENT DOCUMENTS

| 31423 | 7/1981 | European Pat. Off. . |
| 161600 | 11/1985 | European Pat. Off. . |
| 2238319 | 2/1973 | Germany . |
| 1170610 | 11/1969 | United Kingdom . |

*Primary Examiner*—Richard L. Raymond
*Attorney, Agent, or Firm*—Joseph C. Gil

[57] ABSTRACT

The invention relates to a process for the fractionation and purification of aromatic polyamine mixtures and their use.

14 Claims, 4 Drawing Sheets

5,679,840

FRACTIONATION AND PURIFICATION OF AROMATIC POLYAMINE MIXTURES AND THE USE THEREOF

BACKGROUND OF THE INVENTION

The present invention relates to a process for fractionating and purifying aromatic polyamine mixtures and their use.

The production of aromatic polyamines and polyamine mixtures, in particular from the diphenylmethane series, is described in many patent applications and patents, also the use of these products. Great importance is attached to the use of these products as raw materials for the preparation of isocyanates, generally by reacting the polyamine mixture with phosgene by conventional and generally known methods.

In many cases, however, the isocyanates or isocyanate mixtures which result are not produced in the form and composition in which they are preferably utilized in the isocyanate stage but first have to be converted into the form appropriate for their use by means of sometimes complicated working-up and separating procedures. Suitable polyamine precursors, which might be easier to convert into the forms required for use as isocyanates, are in many cases very difficult or even technically impossible to produce, or are not economically viable to produce.

An example is the recovery of 4,4'-diisocyanato-diphenylmethane, which is important for the preparation of high-quality polyurethanes, whose amine precursor can generally be obtained from aniline and formaldehyde only together with isomers, in particular the 2,4'-isomers, and higher functional polyamines. Although these constituents are the basis for equally useful isocyanates, separation of the initial isocyanates into isocyanates or isocyanate mixtures suitable for further processing is not simple. As a rule, some of the binuclear compounds are first separated from the remainder. Then the other isomers in the binuclear fraction are removed from 4,4'-diisocyanato-diphenylmethane in a second distillation step requiring several separating stages.

Recently, the 2,4'-isomer itself, in enriched form, has gained increasing importance as a raw material for polyurethane and can only be enriched, as compared with the 4,4'-isomer, and the optionally present 2,2'-isomer removed, by means of a very complicated distillation procedure. Isomer separation procedures or enrichment procedures within the fraction of higher-nucleated homologues or the higher functional constituents of either amines or isocyanates from the diphenylmethane series are virtually unknown.

4,4'-diamino-diphenylmethane is also increasingly being used as a raw material for di-(4-isocyanatocyclohexyl)-methane, the ring-hydrogenated form of 4,4'-diisocyanato-diphenylmethane, wherein the provision of suitable aromatic polyamine mixtures for the hydrogenation stage, with the highest possible concentration of 4,4'-diamino-diphenylmethane and simultaneously the lowest possible concentration of 2,4'-diamino-diphenylamine, is very expensive.

It is known that amines can be separated in certain cases by partial conversion into their salts, wherein, inter alia, the different base-strengths are utilized. In this event, they are generally monoamines with very different base-strengths. This type of disproportionation effect in two-phase systems has also already been described (German Auslegeschriften 2,238,319 and 2,528,694) for aromatic polyamine mixtures, in particular those from the diphenylmethane series.

The effects, due to the large number of components present in this kind of mixture where the amino groups are of a type which hardly differ at all, virtually all being aryl amino groups, are not particularly large and are not sufficiently pronounced to be of interest for direct use with simple equipment.

The object of the present invention was to provide a process which permits fractionation or purification of aromatic polyamine mixtures in a simple manner so that isomers are produced in a pure form or in an enriched form.

DESCRIPTION OF THE INVENTION

Figure 1:
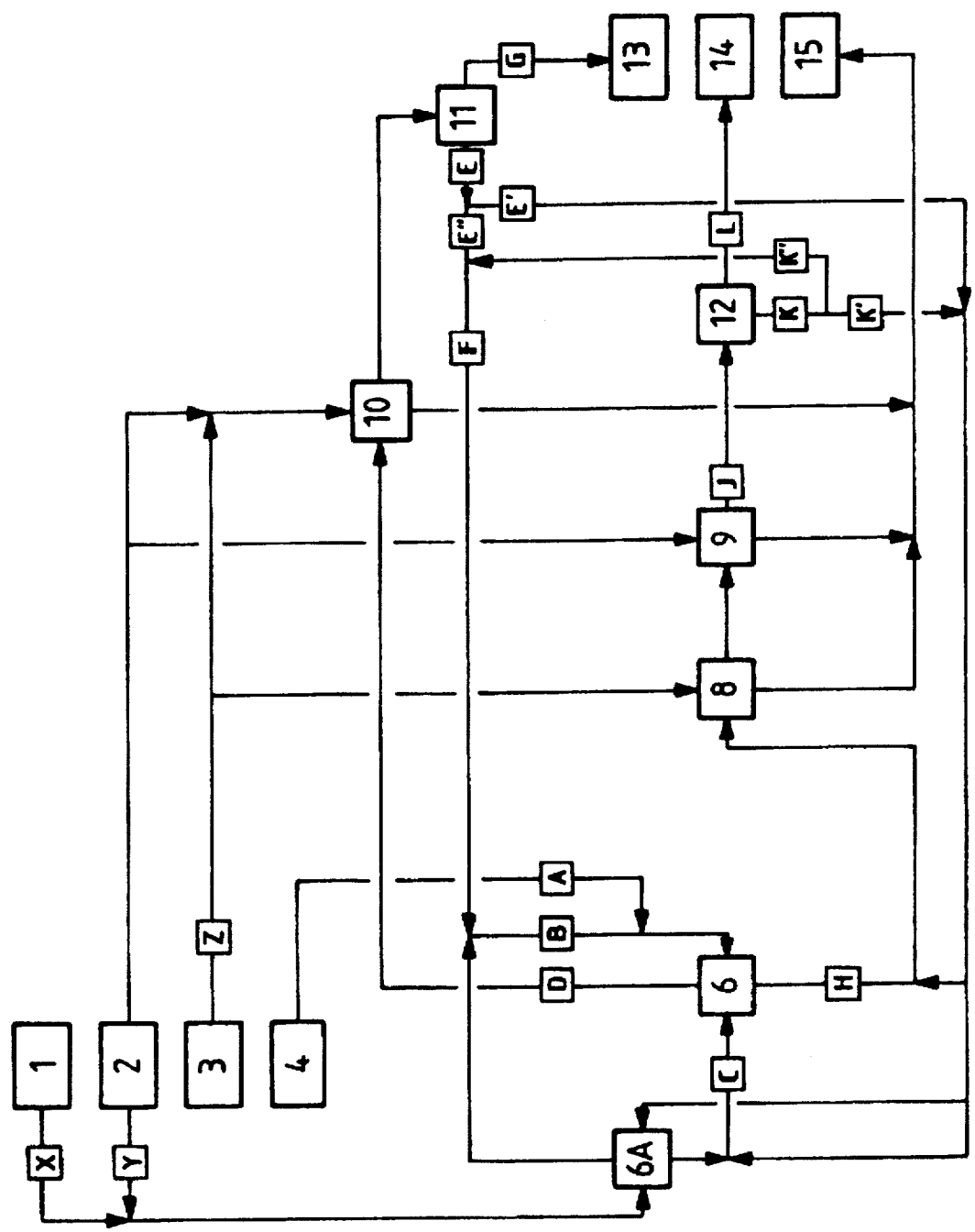
FIGS. 1 through 4 represent flow diagrams for embodiments of the present invention.

The above noted object was achieved by the process according to the invention, which produces a surprisingly high separating power during the fractionation of aromatic polyamine mixtures, in particular from the diphenylmethane series, and whose effect thus extends far beyond the effects disclosed in the prior art.

During fractionation according to the invention of aromatic polyamine mixtures, further polyamine mixtures with different compositions are obtained. These derived polyamine mixtures may be those which are accessible via known synthesis pathways in only a very complicated manner. Thus, they may also be polyamine mixtures which are more suitable for a simplified preparation of isocyanates than known polyamine mixtures which are readily produced in an industrial situation by performing, at the amine stage, the isomer separations which are difficult to perform, for instance, at the isocyanate stage. These types of mixture may also, because they cannot be prepared by the prior art, be completely new polyamine mixtures which lead to completely new isocyanates.

On the other hand, the process according to the invention can be used to obtain product fractions which correspond to standard or to starting polyamines from any polyamine mixtures, i.e. also polyamine mixtures obtained by the recycling of polyurethane plastics, which differ from the originally used polyamines or isocyanates due to contamination or due to the non-statistical, i.e. selective, loss of individual components during recovery.

Finally, the process according to the invention can be used to fractionate secondary products and intermediates not wanted in the end product, which are present as a result of the method of synthesis, by depletion in one product fraction and corresponding enrichment in another fraction, with optional expulsion in a separate fraction.

The present invention is a widely applicable process by means of which the object of fractionating and purifying aromatic di and polyamine mixtures, in particular from the diphenylmethane series, can be achieved.

The invention provides a process for fractionating and purifying aromatic polyamine mixtures, in particular polyamine mixtures from the diphenylmethane series, characterized in that a) the initial polyamine mixture (A) is partitioned in a two-phase system consisting of (i) a hydrophobic solvent phase (B) which essentially consists of aromatic auxiliary amine, which is slightly soluble in water and has a boiling point at atmospheric pressure at least 20° C. below the boiling point of the component with the lowest boiling point in the initial mixture, and optionally polyamines, and (ii) an aqueous phase (C) essentially consisting of an aqueous solution of a strong acid and optionally an auxiliary amine which is at least partly in the salt form, and/or optionally polyamines which are at least partly in the salt form using an extraction stage (6) operating on the counterflow principle with thorough mixing of the phases, by introducing the initial polyamine mixture to extraction stage (6) with the hydrophobic solvent phase (B), with the proviso that the amine equivalents introduced to this two-phase system in streams (A), (B) and (C) always exceeds the number of acid equivalents introduced in stream (C), and the organic phase (D) leaving this extraction stage is at least partly separated, after passage through a washing stage and/or neutralization stage (10), in an optionally multi-stage distillation stage (11), into a distillation fraction essentially consisting of auxiliary amine and a first polyamine fraction produced as distillation residue (G) and aqueous phase (H) leaving the first extradion stage (6)

b) passes, optionally at least partly via an upstream extraction stage (7)

c) into a neutralization stage (8), the acid contained in the aqueous phase being neutralized with bases, preferably aqueous caustic soda solution and is then mechanically separated in a phase separation step into an aqueous phase containing the acid in the form of its neutral salts and an organic phase containing essentially polyamine and auxiliary amine and d) the organic phase (J) produced in neutralization stage (8), optionally after passage through a washing stage (9), is worked up at least partly in an optionally multi-stage distillation stage (12) into a distillation fraction (K) essentially consisting of auxiliary amine and a second polyamine fraction produced as distillation residue (L).

The numbers and capital letters above and used in the description which follows refer to elements and streams shown in the drawings.

The process is preferably performed in such a way that b) the aqueous phase (H) produced in extraction stage (6) is at least partly extracted in an upstream extraction stage (7) operated on the counterflow principle, using an organic phase (O) as extraction agent, consisting of auxiliary amine and optionally polyamine, the latter preferably having the composition of the second subproduct (L) and preferably introduced as one constituent of stream (J), the organic phase (M) resulting from process stage (7) being added to stream (B) and thus taken to extraction stage (6) and the aqueous phase (N) resulting from (7) being taken to neutralization stage (8).

The process according to the invention is performed in particular in such a way that a substream (D") is separated from organic phase (D) leaving extraction stage (6) and is extracted in an optionally multistage extraction stage (5), the first stage preferably being operated as a mixer-settler unit, with at least part of, preferably with all of, stream (X) of the aqueous acid in the countercurrent, optionally with the addition of auxiliary amine, and the size of substream (D") is selected so that as extensive as possible a transfer of polyamine contained in (D") to aqueous phase (Q) leaving the extraction unit (5) takes place, part of or all of the said aqueous phase (Q) being taken to extraction stage (6) as the aqueous phase, directly and/or via mixer (6A), optionally after the addition of water from stream (Y) and/or auxiliary amine and/or further aqueous acid, the organic phase (P) produced in (5) essentially consisting of hydrophobic solvent and optionally auxiliary amine, also being added to organic phase (B) supplied to extraction stage (6) and used as solvent for the initial polyamine (A).

More particularly, the present invention, in its broadest embodiment, is directed to a process for the fractionation and purification of aromatic polyamine mixtures, in particular of polyamine mixtures of the diphenylmethane series, comprising:

a) mixing the polyamine starting mixture (A) in a first extraction stage (6) with a two-phase system comprising
(i) a hydrophobic solvent phase (B) which consists essentially of an aromatic auxiliary amine which is slightly soluble in water and exhibits at normal pressure a boiling point which is at least 20° C. below the boiling point of the lowest-boiling component of the starting mixture, and optionally polyamine, and
(ii) an aqueous phase (C) consisting essentially of water, a strong acid and optionally an auxiliary amine present at least in part in the salt form, and optionally polyamines present at least in part in the salt form,
with said first extraction stage (6) operating on the countercurrent principle, and wherein said polyamine starting mixture (A) is introduced into said first extraction stage with said hydrophobic solvent phase (B), with the proviso that the sum of amine equivalents introduced via polyamine mixture (A), hydrophobic solvent phase (B) and aqueous phase (C) always exceeds the number of acid equivalents introduced via aqueous phase (C), and with the further proviso that a first aqueous phase (H) and a first organic phase (D) exit said first extraction stage (6), b) distilling said first organic phase (D) in first distillation stage (11) into
i) a first fraction (E) consisting essentially of auxiliary amine, and
ii) a distillation residue (G) consisting essentially of a first polyamine fraction, d) neutralizing said first aqueous phase (H) by adding a base thereto (8) and phase separating the resultant mixture into
i) a second aqueous phase containing the acid in the form of its neutral salt, and
ii) a second organic phase consisting essentially of polyamine and auxiliary amine, e) separating said second organic phase in a second distillation stage (12) into
i) a distillate (K) consisting essentially of auxiliary amine, and
ii) a distillation residue (L) consisting essentially of a second polyamine fraction.

The auxiliary amines which are used are generally monoamines such as aniline and/or aniline derivatives carrying substituents. The substituents are preferably $C_1$–$C_2$-alkyl substituents and/or benzyl radicals in the aromatic ring and/or on the nitrogen of the aniline parent molecule. These substances may be used either in the pure form or in the form of isomer mixtures or in the form of technical grade or specifically prepared mixtures with each other. Suitable amines include, for example: N-propylaniline, N,N-dipropylaniline, N-butylaniline, N,N-dibutylaniline, N-isobutylaniline, 2-methylaniline, 2,4-dimethylaniline, N,2-dimethylaniline, N,N,2-trimethylaniline, N-ethyl-2-methylaniline, 3-methylaniline, N,N,3-trimethylaniline, N-ethyl-3-methylaniline, N,N-diethyl-3-methylaniline, N-butyl-3-methylaniline, 3-trifluoromethylaniline, 4-methylaniline, N,4-dimethylaniline, N,N,4-trimethylaniline, N-ethyl-4-methylaniline, N,N-diethyl-4-methylaniline, 2-ethylaniline, 4-ethylaniline, xylidine, 2-isopropylaniline, 2-ethyl-6-methylaniline, 2,4,5-trimethylaniline, 2,3,5-trimethylaniline, 4-tert.-butylaniline, 2-ethyl-4,6-dimethylaniline, 2,6-diethyl-4-methylanifine, 2,6-diisopropylaniline, 4-cyclohexylaniline, 4-cyclohexyl-2-methylaniline, 2-methoxyaniline, 2-methoxy-N,N- dimethylaniline, 2-trifluoromethylaniline, 2-ethoxyaniline, 3-methoxyaniline, 3-ethoxyaniline, 3-ethoxy-N,N-diethylaniline, 4-methoxyaniline, N-methyl-p-anisidine, 5-methoxy-2-methylaniline, 2-methoxy-5-methylaniline, 2-ethoxy-5-methylaniline, 2,4-dimethoxyaniline, 2,5-dimethoxyaniline, 5,6,7,8-tetrahydronaphthylamine (1 or 2).

Aniline, 2,6-dimethylaniline, 2,6-diethylaniline, 2-methyl-6-ethylaniline, mesidine, N-methylaniline, N-ethylaniline, N,N-dimethylaniline, N,N-diethylaniline, amino-diphenylmethane are preferably used as auxiliary amine.

The polyamine mixtures from the diphenylmethane series used are preferably those like the ones produced during acid-catalyzed condensation of aniline and formaldehyde. This type of treated polyamine mixture, thus the fractions obtained using the process according to the invention, is used to prepare the corresponding aromatic polyisocyanate mixture and for the preparation of polyurethane plastics. In addition, fractions obtained by the process according to the invention are used to prepare the corresponding ring-hydrogenated polyamines or as cross-linking agents and as epoxide hardeners. The corresponding polyisocyanates prepared from the fractionated polyamine mixtures are preferably used to prepare polyurethane foams.

The initial mixtures are, for example, industrial arylamine mixtures such as those produced during preparation of the starting compounds or such as those obtained during recovery procedures. Examples of arylamine mixtures for which fractionation and purification by the process according to the invention is ideally suited, are 1. polyamine mixtures from the diphenylmethane series, such as those arising during the condensation and acid-catalyses rearrangement of aniline and formaldehyde,
2. polyamine mixtures from the diphenylmethane series such as those produced during the acid-catalyses condensation of substituted anilines and formaldehyde,
3. polyamine mixtures from the diphenylmethane series such as those produced during the mixed condensation of substituted anilines with each other and/or with aniline and formaldehyde,
4. polyamine mixtures from the diphenylmethane series such as those produced during the condensation, also the mixed condensation, of substituted anilines and/or aniline with aldehydes and/or ketones,
5. polyamine mixtures from the diphenylmethane series such as those arising during the nitration and subsequent reduction of di and/or polyarylmethanes and/or substituted di and/or polyarylmethanes; here, polyarylmethanes are understood to be in particular the benzyl homologues of diphenylmethane,
6. polyamine mixtures from the diphenylmethane series such as those arising during the condensation of monoarylmonoamines (e.g. aniline, substituted anilines) and/or monoaryldiamines (phenylenediamine, substituted phenylenediamines) with aldehydes, ketones, in particular formaldehyde, and acid-catalyses rearrangement and
7. polyamine mixtures from the triphenylmethane series such as those arising, for instance, during nitration and subsequent reduction of triphenylmethane, in particular alkyl-substituted triphenylmethanes, and its higher-nucleated homologues, in particular benzyl homologues.

The acids used am water-soluble proton acids with a pKA value of less than 2.5, preferably less than 1.5. Examples of these are hydrochloric acid, hydrobromic acid, sulfuric acid, trifluoroacetic acid, methanesulphonic acid or phosphoric acid. Hydrochloric acid and sulfuric acid are preferably used. The acids mentioned may also be used as a mixture with acid or neutral salts of this type of acid, such as, for example, the corresponding ammonium salts or also the corresponding alkali metal salts. In general, the acids mentioned are present in aqueous phase (C) either as an aqueous solution of the free acid or as an aqueous solution which also contains, in addition to the free acid, the ammonium salt of the acid with auxiliary amine and/or polyamine, or as an aqueous solution in which the acid is present entirely in the form of its ammonium salt with auxiliary amine and/or polyamine and which optionally contains further auxiliary amine which is not bonded in a salt-like manner.

At the latest after passage through extraction stage (6), the acids mentioned are present in the aqueous phase in the form of the ammonium salt of the acid with the fraction of polyamine found in the aqueous phase and with auxiliary amine.

After passage through the extraction stage, optionally extraction stages, the acid in the aqueous phase is converted into the corresponding neutral salt by neutralizing with strong bases. This releases the polyamines and auxiliary amine which were bonded in a salt-like manner.

The process according to the invention may be performed either batchwise or continuously. The preferred embodiment is a continuous mode of operation. In this case, the process is performed at all stages under the system's own inherent pressure and preferably in an inert gas atmosphere (nitrogen).

Figure 2:
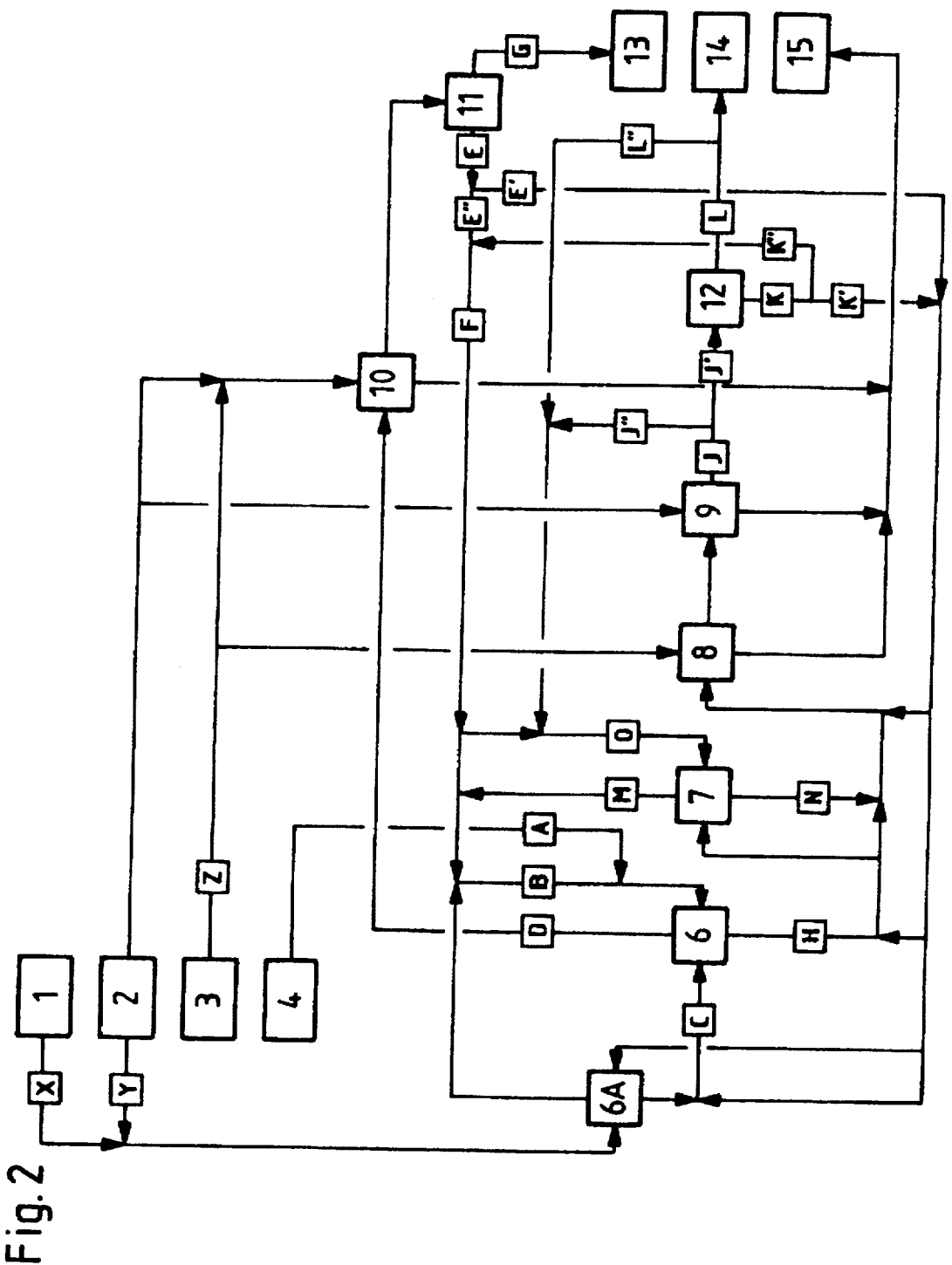
Figure 3:
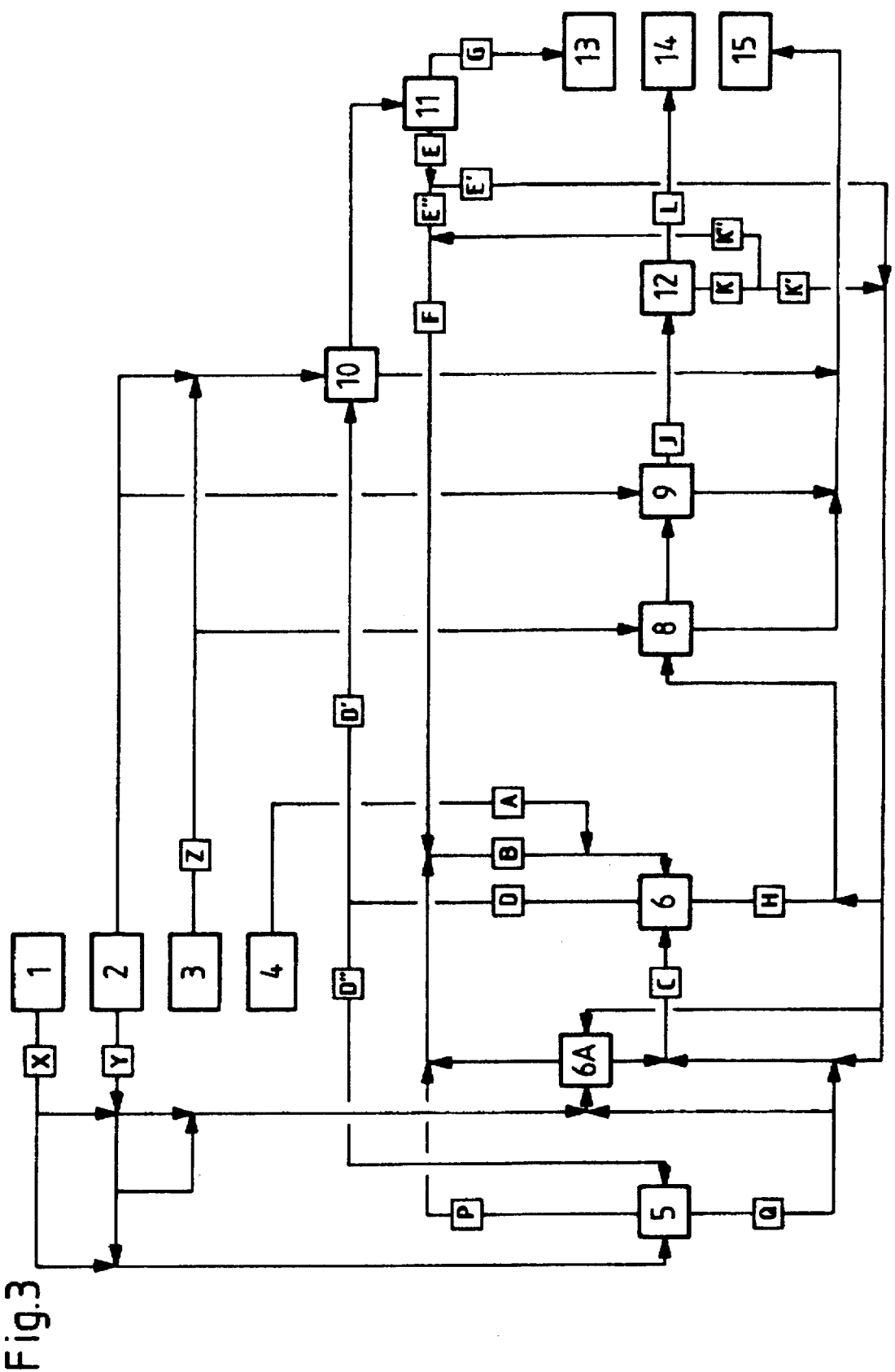
Figure 4:
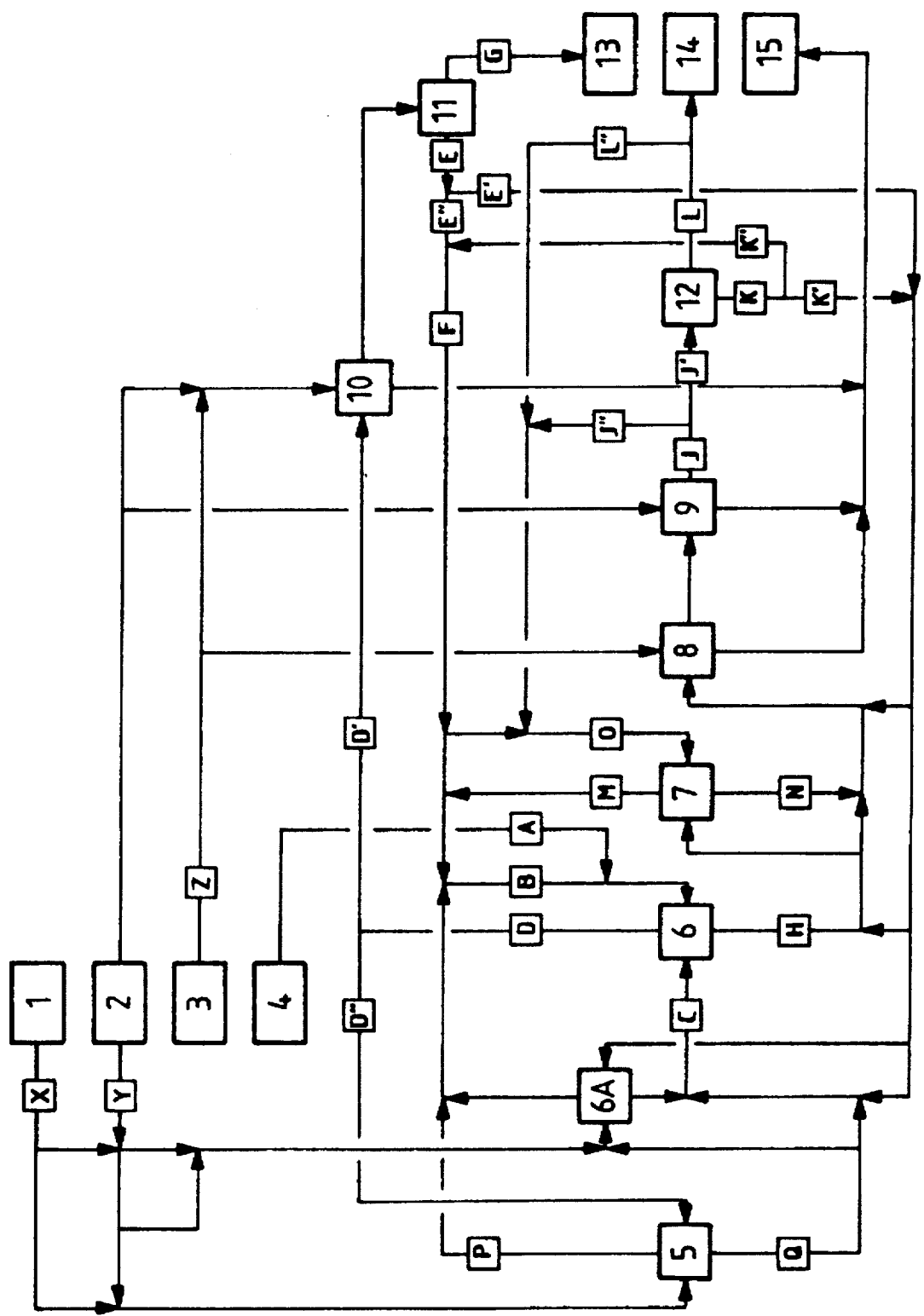

The process according to the invention may be performed with one (FIG. 1), two (FIGS. 2 and 3) or three (FIG. 4) extraction stages.

The process according to the invention may be repeated to increase the enrichment or corresponding depletion effect with each of the product fractions produced.

The flow-charts shown in FIGS. 1 through 4 are used to explain the process according to the invention in more detail. In these figures the following key is used:

(1) a tank for aqueous acid
(2) a tank for water
(3) a tank for aqueous base
(4) a tank for the initial polyamine
(5) a single or multi-stage extractor which generally comprises the first stage of a mixer-settler unit from the point of view of the aqueous phase
(6A) a mixer or a mixer-settler unit
(6) a (first) extraction stage
(7) a (second) extraction stage
(8) a neutralizing stage
(9) a washing stage
(10) a washing and/or neutralizing stage
(11) a first, optionally multi-stage operated, distillation stage
(12) another, optionally multi-stage, operated distillation stage
(13) a tank for a first process product
(14) a tank for another process product
(15) a tank for waste water The letters A–Q, X, Y and Z represent the streams to which reference is made in the following and in the examples.

Extraction stage (5) is, in the simplest case, a single stage mixer-settler unit, preferably, however, multi-stage extraction units are used, wherein the first stage from the point of view of stream, (X) generally comprises a mixer-settler unit.

Extraction stage (6A) is, in the simplest case, a mixer or a mixer-settler unit.

Extraction stage (6) is, in the simplest case, a single stage mixer-settler unit, preferably, however, multi-stage extraction units are used.

The optional upstream extraction stage (7), in the simplest case, also comprises a mixer-settler unit, preferably, however, multi-stage extraction units are also used here.

Multi-stage extraction units may comprise several extractors connected in series. Conventional counterflow extraction devices are preferably used.

Neutralization stage (8) is a device for intensive thorough mixing of aqueous phases (H) and (N) in order to react the acids contained therein with an aqueous solution of an excess of a strong base (Z) from container (3) with the possibility of removing the heat of neutralization and then isolating the polyamine.

For thorough mixing, in the simplest case, one or several stirred tanks are used and the mixing process can be amplified by means of mixing nozzles, intensive mixers and/or recirculating devices. In the simplest case, separators are used for subsequent phase separation, wherein phase separation may be intensified by the incorporation of separating aids. Also suitable are, for example, centrifuges.

In cases in which simple mechanical separation is difficult or impossible after reaction of aqueous phases (H) and (N) with strong bases, separation is performed by using additional auxiliary amine or optionally water, optionally as an extraction process in a preferably multi-stage extractor.

Washing stage (9) is, in the simplest case, a mixer-settler unit in which stream (J) is washed with water, washing stage (9) not being basically required for implementation of the process according to the invention, but generally being advantageous.

Washing and/or neutralizing stage (10) is also, in the simplest case, a mixer-settler unit, multi-stage extractors, however, preferably being used.

In process stage (10), the organic phase (D) may be reacted with both water and also preferably with dilute aqueous solutions of strong bases to remove all the acid.

When performing process stage (10) purely as a washing stage using water, the resulting aqueous phase is not added to the waste water after it has been separated but is returned to a suitable point in the process.

Distillation stages (11) and (12) each comprise, in the simplest case, a distillation column in which each particular feed product (is separated) into a distillation product consisting of auxiliary amine and a distillation residue consisting in the case of distillation stage (11) of a first polyamine fraction (G) and in the case of distillation stage (12) of a second polyamine fraction (L).

Use of an energy-saving multi-stage distillation in stage (11) and/or (12) is particularly preferred if the associated additional technical expenditure is economically justified. The distillates produced may be combined and mixed with each other before re-use.

When performing neutralization stage (8) using additional auxiliary amine as solvent, the feed product for distillation stage (12) generally contains considerable amounts of auxiliary amine which are generally separated together as distillation fraction (K) from the second polyamine fraction (L) produced as distillation residue.

The process according to the invention can be performed in several technical variants.

In accordance with a first variant, feeding the initial polyamine mixture (stream A) from container (4) is performed by mixing it with stream (B) consisting of auxiliary amine.

After adding the initial polyamine (A) to stream (B) the concentration of polyamine is generally 5–90 wt. %, preferably 10–60 wt. %.

Feeding the acid (stream X) takes place via aqueous phase (C). In general, stream (C) consists of water, a strong proton acid and optionally auxiliary amine and/or optionally polyamine. In general, the acid in aqueous phase (C) is present as an aqueous solution of the acid which optionally contains ammonium salts of the acid with the auxiliary amine and/or polyamine. The acid is preferably present as an aqueous solution of its ammonium salts with auxiliary amine and/or polyamine which optionally contains dissolved free auxiliary amine and/or polyamine, i.e. amines not bonded in a salt-like manner.

After that, it is perfectly possible, and to achieve a specific separation task also advantageous, to feed stream (C) to stage (6) entirely without auxiliary amine, simply as an aqueous acid with a definite concentration, provided the boundary condition applying to process stage (6) in each case is satisfied, according to which the sum of the amine equivalents introduced in streams (A), (B) and (C) always exceeds the number of acid equivalents introduced in stream (C).

In a preferred embodiment, in addition to aqueous acid (X) and optionally additional water (Y), auxiliary amine is supplied to process stage (6A) in an amount such that the desired amine/acid ratio is established in the aqueous phase leaving stage (6A).

It is not of crucial importance to the process according to the invention, in the case of the formation of a two-phase mixture in the mixer in process stage (6A), whether this is fed as such to the first stage, from the point of view of the aqueous phase, of extraction stage (6) without prior phase separation, but it is advantageous if stage (6A) is designed as a mixer-settler unit in the case of the formation of a two-phase mixture and only the separated aqueous stage is taken to (6) and the separated organic phase is added to stream (B).

It has proven to be expedient to define the acid content of the aqueous phase independently of the amine concentration being established in the aqueous phase of a two-phase system, which depends on the process parameters (e.g. composition of the organic and aqueous phases, phase ratio, temperature), by using a so-called "molarity". The "molarity" is defined as a theoretical concentration of 100% protonated amine (i.e. the same number of acid and amine equivalents) in a volume arithmetically reduced by the amount of non-protonated amine or optionally in a volume of aqueous phase arithmetically increased by an amount of amine corresponding to full bonding to the acid in the form of ammonium salts.

The molarity defined in this way can have different values depending on the process parameters, in particular the type of auxiliary amine, and is specifically varied within this range depending on the separating task on which the particular embodiment is based, in this case product-specific.

The acid content of stream (C) which is well-defined, and measured and controlled within narrow limits, for the particular embodiment of the process according to the invention is specifically varied within a wide range, either overall or in individual process steps, as an important reference variable depending on the separating task on which the particular embodiment is based, here product-specific, by optionally supplying water from stream (Y) or aqueous acid from stream (X).

This working range has an upper threshold which is restricted in practice on the one hand by the increasing tendency of the ammonium salt to crystallize with increasing concentration and on the other hand by the increasing mutual solubility of the phases in each other.

The working range of the process according to the invention with respect to molarity has a lower threshold which is governed by economics. As the acid content decreases, the separating power is quantitatively lowered, i.e. for outstanding qualitative separating power and lack of technical problems, with decreasing molarity an increasingly large volume of aqueous phase is required to separate a given amount of amine.

The degree of protonation gives the ratio of acid equivalents to amine equivalents.

In preferably multi-stage extraction stage (6), organic phase (B) and aqueous phase (C) are supplied in counterflow to each other with intimate and thorough mixing.

During this procedure a transfer of polyarylamine generally takes place from organic phase (B) into aqueous phase (C), optionally in exchange for arylamine in the opposite direction.

In the aqueous phase (H) leaving extraction stage (6), the acid is present as an aqueous solution of its ammonium salts with polyamine and optionally auxiliary amine, which generally also contains some free, i.e. not bonded as a salt, polyamine and optionally free, i.e. not bonded as a salt, auxiliary amine.

The initial polyamine (A) introduced together with organic phase (B) to extractor (6) is partitioned between the aqueous phase (H) leaving the extractor and the organic phase (D) leaving the extractor (6) (quantitative fractionation).

Partition by amounts of the individual components from the initial polyamine mixture between the resulting aqueous phase (H) and the resulting organic phase (D) takes place, under the conditions in the process according to the invention, with surprisingly high selectivity so that the resulting product fractions have a different composition, in some circumstances differing greatly, from that of the initial polyamine mixture (qualitative fractionation).

For example, starting with the preferably used aniline/formaldehyde condensation products, it was found that if a polyamine component contained in the initial mixture is present in two or more isomeric forms, as a rule the orthoisomeric form(s) is (are) relatively enriched in organic phase (D) leaving separation stage (6); for example 2,4'-diamino-diphenylmethane relative to 4,4'-diamino-diphenylmethane. Conversely, the resulting aqueous phase (H) is relatively depleted in the 2,4'-isomer whereas the 4,4'-isomer is relatively enriched.

If several "ortho" isomers are present in the initial polyamine, e.g. 2,2' and 2,4'-diamino-diphenylmethane, then the "high-ortho" 2,2'-isomer is more strongly enriched in organic phase (D) as compared with the "low-ortho" 2,4'-isomer, the latter for its part being relatively enriched as compared with the "even lower ortho" 4,4'-isomer.

The enrichment/depletion effect initially found for aniline/formaldehyde condensation products in the diamino-diphenylmethane series is associated purely empirically and descriptively with the criterion of ortho and para substitution. Characterization of the process products as "high-ortho" and "low-ortho" as deduced from this behavior is therefore relative and is expressed by the term "degree of ortho-substitution".

The "degree of ortho-substitution" is therefore defined as the ratio of those amino groups and methylene groups which are located in an ortho position with respect to each other to the total number of all amino group/methylene group relationships. This term can be applied to virtually all isomer separations in the case of polyamines which are prepared from arylamines, even substituted arylamines, using carbonyl compounds in aqueous acid medium.

Surprisingly, the same enrichment/depletion effect, governed by the degree of orth-substitution, has now also been found for the well-characterized and analytically identifiable isomeric three-ring compounds from aniline/formaldehyde condensation.

Separation of the isomers of condensation products of formaldehyde and aniline is analogous to that of diaminoaryl compounds such as phenylenediamine or alkyl-substituted phenylenediamines.

The polyamine mixtures mentioned hitherto have, as a result of their method of preparation, amino groups which are located in virtually only the ortho and/or para position with respect to methylene groups. Thus, within a group of isomeric compounds, generally those with the higher degree of ortho-substitution are enriched in organic phase (D) during fractionation, as compared with isomers with a lower degree of ortho-substitution.

Polyamine mixtures, in particular those from the diphenylmethane series, including particular higher-nucleated homologues which are prepared by other methods, for example by nitration of diphenylmethane or methyldiphenylmethanes and subsequent reduction, also have, in addition to ortho and para amino groups, as a result of the method of preparation, other amino group/methylene group relationships. The process according to the invention is equally effective for these polyamine mixtures. For instance, a polyamine mixture can be prepared from a mixture of 2- and 4-methyldiphenylmethane by nitration and subsequent reduction which mainly consists of an isomeric mixture of

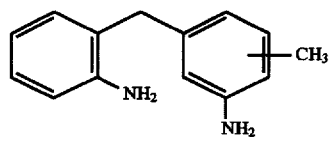

and

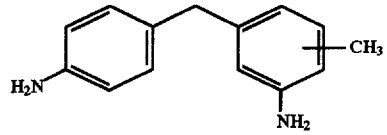

During fractionation of this type of mixture using the process according to the invention, the 3,2'-amino isomers are enriched in the organic phase (D) as compared with the 3,4'-amino isomers.

The criterion "high ortho" and "low ortho" or "degree of orthosubstitution" in these polyamine mixtures no longer covers all the isomers and therefore has to be applied logically, instead of using the terms "in the ortho position" and "in the para position", by classifying the isomers into those with smaller (ortho) and those with larger (para) spatial distances between amino groups, these generally being located in different six-membered rings, and methylene bridges or between one amino group and another.

A further class of aromatic polyamine mixture which can be fractionated very effectively by means of the process according to the invention, comprises polyamines from triphenylmethane and its higher-nucleated homologues, preferably benzyl homologues such as are produced, for instance, by nitration and subsequent reduction of the corresponding hydrocarbon mixtures.

When fractionating industrial polyamine mixtures of the last named class of substances I. mixed condensation products of mono and diaminoaryl compounds with formaldehyde or in general carbonyl compounds II. polyamine mixtures from processes by means of nitration and subsequent reduction of diphenylmethane and preferably substituted, in particular alkyl-substituted, diphenylmethanes and the relevant homologues and III. polyamine mixtures from processes by means of nitration and subsequent reduction of triphenylmethane and preferably substituted, in particular alkyl-substituted, triphenylmethanes and the relevant higher-nucleated benzyl homologues in addition to purely isomeric separation, a further surprising selectivity was found.

Polyamine mixtures of the substance classes I to III mentioned above contain or may contain components in which at least one aryl ring or molecule carries more than one, generally two, amino groups. These components may be the preferred constituents in the polyamine mixture without having to be the major product by amount, as a result of the method of preparation.

In order better to characterize this type of component, the expression "degree of amino-substitution" is used, with which primarily the number of amino groups in a component in proportion to the number of aryl rings is characterized. For aniline and its condensation products with formaldehyde, this expression is always 1.0, for phenylenediamine and its condensation products it is always 2.0. For purely mixed condensates, the value 1.5 is produced for diphenylmethane isomers and values between >1.0 and <2.0 are produced for the higher-nucleated homologues. Statistical application of the term degree of amino-substitution to characterize industrial polyamine mixtures also produces values between 1.0 and 2.0.

When fractionating polyamine mixtures with a degree of amino-substitution of >1.0, it has now been found that components with a higher degree of amino-substitution are relatively enriched in the resulting aqueous phase (H), in fact the more so the higher the degree of amino-substitution.

Independently of that, separation is also effected here in accordance with the degree of ortho-substitution. Thus, the process according to the invention also opens up for this class of substance, a new route to decoupling the form of the raw material prepared (amine stage) and the form of the end product used (isocyanate stage) by fractionation and/or enrichment of the amine stage and separate further processing of the fractions so that separate optimization of the two stages is facilitated, enabling the recovery of completely new isocyanate mixtures or making this possible for the first time in cases where hitherto there have been no suitable processes and methods or where these have not really been practicable.

These "achievements" are supplemented by a further selectivity criterion, which was found during fractionation of industrial polyamine mixtures, in particular those with higher-nucleated homologues, and which relates to the "nuclearity" of the polyamine mixture. The term "nuclearity" expresses primarily the number of aryl units in a component in an aromatic polyamine mixture. In a wider sense, the term nuclearity is used to express the statistical average nuclearity of the total mixture in a polyamine mixture consisting of numerous components, each of which has an exact number of rings.

Particularly surprisingly, it was now found that when fractionating polyamine mixtures with higher-nucleated fractions, in particular when fractionating industrial mixtures of aniline/formaldehyde condensates, those mixtures could also be fractionated in accordance with the criterion of nuclearity.

In particular, a low molarity in aqueous phase (C), within the molarity range which can be used according to the process, led to a relative enrichment of higher-nucleated components in organic phase (D).

The surprising finding can be extended and stated more precisely to the effect that relative enrichment and depletion also takes place within the higher-nucleated homologues themselves. If, for example, in an industrial mixture of diamino-diphenylmethanes in which in one fraction the three-ring component is relatively enriched or depleted as compared with the two-ring component, then there is also a relative enrichment or depletion of four-ring components as compared with three-ring components found, i.e. a still stronger relative enrichment or depletion, likewise of five-ring components as compared with four-ring components, and so on.

As a result of this and of the simultaneous isomer separation, always proceeding in the direction of a relative amplification of the "degree of ortho-substitution" in organic phase (D), and of the possibility of repeating the separation according to the invention with individual product fractions, optionally with modified process parameters, numerous possibilities are produced, starting from known and readily accessible polyamine mixtures of obtaining, via the process according to the invention, less readily accessible or completely new, because they have hitherto been inaccessible using the prior art, polyamines and thus polyisocyanates. This applies in particular to products from the diamino and diisocyanato-diphenylmethane series and quite particularly to polyamine and polyisocyanate mixtures with an extremely high proportion of higher-nucleated components.

Enrichment or depletion generally becomes more effective with an increasing degree of protonation in the aqueous phase of the separating stage.

In addition, the process according to the invention has also proved to be of general effectiveness when applied to other structurally similar polyamines. Thus, for example, the polyamine mixtures already mentioned, which have been obtained by nitration of di and polyarylmethanes and subsequent reduction, may also contain, monoaminopolyarylmethane compounds or components in which one or more methylene groups have been converted into keto and/or hydroxymethylene groups in side reactions and thus into unwanted secondary products.

During the condensation of arylamines with carbonyl compounds, numerous incompletely rearranged intermediates and secondary products may be produced. During fractionation of the polyamine mixture containing them, most of these compounds are generally subject to enrichment in one of the resulting fractions so that the effect can be utilized for separation and fractionation.

Optionally, these types of product may be enriched in this way or they may in their turn be fractionated as specifically prepared polyamine mixtures such as, for instance, polyaminobenzophenones or aminobenzylarylamine mixtures.

The organic phase (D) leaving extraction stage (6) contains, inter alia, varying amounts of acid, depending on the auxiliary amine used, which are removed before distilling stream (D).

In the simplest case, this takes place in process stage (10) by washing with water and/or by neutralizing with excess, dilute aqueous bases, for example dilute caustic soda solution.

Organic phase (D) or (D') is transferred to distillation stage (11) after passage through stage (10).

In the last stage of optionally multi-stage distillation stage (11), the first polyamine subproduct (G) is separated and collected in process product tank (13).

The corresponding second subproduct is found in aqueous phase (H) leaving extraction stage (6).

Aqueous phase (H), optionally after the addition of auxiliary amine, is reacted in neutralization stage (8) with the aqueous solution of a strong base, preferably caustic soda solution, to neutralize the acid contained therein.

The aqueous phase produced during neutralization is separated and collected in waste water container (15).

The organic phase produced during neutralization is separated as stream (J), optionally washed with water in washing stage (9) and worked up in distillation stage (12).

In the last stage of optionally multi-stage distillation stage (12) the second polyamine subproduct (L) is separated and collected in process product tank (14).

Using this variant of the process according to the invention, considerable separating power is produced during the fractionation of polyamine mixtures and numerous separation problems are satisfactorily solved.

In particular, in the first polyamine fraction (G), the relative enrichment of the components preferentially contained in this fraction can be specifically varied and maximized.

The proportion of these components remaining in the second polyamine fraction (L), however, are not minimized in an equivalent manner in accordance with this first variant, but are relatively depleted in a variable manner only down to a concentration whose lower limit depends on the characteristic partition equilibrium, for the particular process parameters, of the polyamine components from (A) between organic phase (B) on entering extractor (6) and aqueous phase (H) on leaving extractor (6).

By admixing amounts of the second polyamine fraction (L) either as a substream of (J) or as a substream of (L) to the initial arylamine (A), its relative concentration of components of (G) can be lowered and thus the lower limit of these components in the second subproduct (L) achievable according to this first variant can be shifted via the partition equilibrium. The only slight improvement in separating power produced in this way may be sufficient for certain applications, but it generally places a restriction on the throughput of (A).

A second variant of the process according to the invention is more advantageous and is preferred as an embodiment. In this variant, in addition, the relative enrichment of the components preferentially contained in second polyamine fraction (L) can also be specifically varied, largely independently of the first product fraction, by extracting the aqueous phase (H) produced in extraction stage (6), or at least some of it, in a downstream extraction stage (7) operating on the counterflow principle, using organic phase (O).

Organic phase (O) consists in general of auxiliary amine and optionally polyamine, the latter preferably having the composition of the second process subproduct (L).

Use of an organic phase (O) without polyamine results in a polyamine fraction in the aqueous phase (N) leaving extraction stage (7) in which the relative enrichment of the components preferentially contained in this phase is specifically increased and maximized beyond the enrichment produced in aqueous phase (H), and the concentration of the components enriched in (G) can be minimized, at the expense of the polyamine concentration in the aqueous phase.

With polyamine as a constituent of organic phase (O), phases (M) and (N) leaving process stage (7) have a higher polyamine concentration than use of an organic phase (O) without polyamine, which is energetically more favorable for implementation of the process according to the invention.

By means of the preferred use of a polyamine with the composition of the second subproduct (L) as a constituent of organic phase (O), the relative enrichment of the polyamine components preferentially contained in the aqueous phase (N) leaving separating stage (7), and thus the second polyamine fraction (L), can be varied and maximized at a higher and thus advantageous concentration due to establishing an equilibrium with self-amplification of the separating effect.

In the simplest and general case, organic phase (O) is formed from at least a substream of stream (F) and optionally further auxiliary amine and/or polyamine, for example a substream of (L). Similarly, stream (O) may be formed from a substream of (F) and a substream (J") of stream (J), containing polyamine mixture (L) in addition to optional auxiliary amine. By means of the possible addition of auxiliary amine, described elsewhere, before or in neutralization stage (8), an organic phase (J) is produced with a composition which corresponds by and large to organic phase (O), so that it can be used, preferably after passage through washing stage (9), as substream (J"), directly and virtually without any further additives, as organic phase (O) in process stage (7).

The molarity of the aqueous phase used in downstream extraction stage (7) is in general greater than that of aqueous phase (H) leaving extraction stage (6). Basically, it is possible, however, to modify both the molarity and the degree of protonation, to improve the separating power according to the process, by adding aqueous acid and/or water, optionally also auxiliary amine, to the aqueous phase.

Basically, it is also possible to increase the molarity by removing water from (H) in a distillation procedure.

Organic phase (M) resulting from stage (7) is added to organic phase (B) used in extraction stage (6).

Aqueous phase (N) resulting from stage (7) is taken to neutralization stage (8).

Using the second variant of the process according to the invention, the relative enrichment or depletion of the two polyamine fractions finally produced can be specifically varied and maximized. In addition to this qualitatively high versatility and power, the second variant also offers, at least for the second polyamine fraction (L), an energetically favorable embodiment. The expense associated with recovering the first polyamine fraction (G) increases more, however, in relative terms the smaller is the amount of (G) with respect to polyamine mixture (A) used, because the remaining concentration of polyamine (G) is correspondingly lower in organic phase (D) which has to be worked up by distillation.

The effect is particularly useful if the components separated with (G) are present in only low concentration in the initial mixture (A) and/or are relatively highly enriched in fraction (G), e.g. during separation according to the invention of polyamine mixtures from the diphenylmethane series.

A partial introduction of initial polyamine (A) to separation stage (6) via aqueous phase (C) generally causes an increase in the polyamine concentration in (D) and thus a decrease in energy requirements. When implementing the process, however, this reduction is associated with a worsening in the qualitative separation results for the first subproduct (G), due to the establishment of an equilibrium between the polyamine in aqueous phase (C) and the polyamine in organic phase (D), so that use is made of this possibility only to a small extent or in cases where there are correspondingly low requirements with respect to separation results.

The third variant of the process according to the invention is an embodiment which is improved in this respect. Starting from the first variant, this is extended to the effect that organic phase (D) leaving process stage (6), containing a reduced concentration of the first subproduct (G) as compared with the concentration of (A) in (B) is divided into stream (D'), which is taken to processing stages (10) and (11) with the objective of continuing to recover polyamine fraction (G), and stream (D").

Stream (D") is reacted, in upstream extraction stage (5), with at least some of, preferably with all of, the aqueous acid, available in stream (X). The extraction is optionally performed as a multi-stage counterflow extraction.

The size of stream (D") taken to extractor (5) is selected so that as extensive as possible, preferably virtually quantitative, transfer of the polyamine contained in organic phase (D") to the aqueous phase leaving extractor (5) takes place during reaction with stream (X).

If the sum of the acid equivalents introduced in process stage (5) exceeds that of the amine equivalents, transfer of the amines to the aqueous phase takes place virtually quantitatively in fact in a single process stage so that no organic phase (P) is produced. The presence of free acid in the resulting aqueous phase has no effect on the progress of the process.

Even in the event that there is an excess of amine equivalents in (D") as compared with acid equivalents in (X), and even with a restricted excess of polyamine equivalents in (D") as compared with acid equivalents in (X), an organic phase (P) which is sufficiently depleted in polyamine for the purposes of the process according to the invention can be obtained by using several stages in upstream process stage (5) and by working with a counterflow system.

In general, the highest permissible concentration of polyamine in (P) is governed by the qualitative requirements placed on the process product in accordance with the particular separating task, i.e. the quality of separation, in the case of variant 3 in particular on process subproduct (L). Maintaining the concentration of polyamine which is relevant to the quality of (L) is regulated within the scope of the operating conditions by exhausting the available acid potential via the selected size of substream (D").

The residual amount of polyamine in organic phase (P) leaving process stage (5) is generally <5 wt. %, preferably <1 wt. %.

From a quantitative point of view it is of advantage to the process and in particular to upstream process stage (5) that the ratio of (D") to (D') tends to higher values, i.e. that (D") becomes larger by amount, as the ratio by amount of polyamines fractions (G) to (L) becomes smaller, because (L) becomes larger at the expense of (G). With increasing amounts of the second polyamine fraction (L) the amount of acid (X) used, and thus available for the extraction of (D") in (5), increases.

Organic phase (P) leaving process stage (5), which is depleted in polyamine, preferably virtually completely depleted of polyamine, is added to organic phase (B) and taken to process stage (6), together with this, as solvent for the initial polyamine (A).

Aqueous phase (Q) leaving process stage (5) contains, in addition to the aqueous acid used, polyamine whose composition largely corresponds to the polyamine separated in (D) and isolated as fraction (G) and optionally auxiliary amine.

In the simplest case, the aqueous phase leaving process stage (5) is taken directly to process stage (6) as stream (C). Aqueous acid and/or water (Y) and/or auxiliary amine are optionally admixed, preferably via mixer (6A).

The addition of a limited amount of initial polyamine (A) to aqueous phase (Q) is also possible, incurring only a small loss of qualitative separating power (relative enrichment) as compared with variant 1, but with improved quantitative power (greater economic viability).

In a further fourth variant, upstream process stage (5), and the advantages produced by its use, is combined with the embodiment of the process according to the invention described as variant 2, which then produces a similar improvement with respect to the first subproduct as does variant 3. As an additional easing of the procedure and simplification when performing process stage (5), it has been proved that the requirements placed on the polyamine concentration remaining in organic phase (P) resulting from (5) are less stringent because the disadvantageous effects of a high polyamine concentration in (P) on the quality of the second subproduct (L) can be compensated for by the downstream extraction stage (7).

The concentration of polyamine in organic phase (P) leaving process stage (5) is therefore generally <5 wt. %, preferably <3 wt. %.

The invention is further illustrated but is not intended to be limited by the following examples in which all parts and percentages are by weight unless otherwise specified.

EXAMPLE

In the mixer section of mixer-settler unit (6A), 1.500 kg/h of 30% strength hydrochloric acid (stream X), 3.300 kg/h of water (stream Y) and 2.650 kg/h of 2,6-dimethylaniline are mixed with each other. Then, in the settler section of stage (6A), the supernatant organic phase (0.700 kg/h) is separated at 85° to 90° C. and supplied to stream B. The remaining aqueous phase is passed in counterflow, as stream (C) with the following composition Stream (C) 29.1% 2,6-dimethylaniline (6.751 kg/h) 6.6% hydrogen chloride 64.3% water, in the subsequent multi-stage extractor (6) at 90° C., against an organic phase which is formed by mixing initial polyamine (A) [stream (A) –1.900 kg/h] with stream (B).

Stream (B) is formed from the organic phase separated in (6A) consisting essentially of 2,6-dimethylaniline and from the organic phase resulting from subsequent stage (7) (stream M).

Stream (B) 16.0% polyarylamine (6.500 kg/h) 83.2% 2,6-dimethylaniline 0.3% hydrogen chloride 0.5% water The organic phase resulting from stage (6) (stream D) has the following composition:

Stream (D) 10.2% polyarylamine (7.907 kg/h) 83.8% 2,6-dimethylaniline 0.5% hydrogen chloride 0.5% water Stream (D) is washed with excess dilute caustic soda solution (substream of Z) and water from container (2) in neutralization stage (10). The aqueous phase is collected in tank (15) as waste water.

The acid-free washed stream (D) is separated in subsequent distillation stage (11) into a distillation fraction (E) at 7.020 kg/h, consisting essentially of 2,6-dimethylaniline, and a distillation residue, which is collected in tank (13) as stream (G) at 0.810 kg/h, this representing the first polyamine fraction.

Subsection (E") of distillate (E) is taken to process stage (7) as stream (O).

The aqueous phase (H) leaving extractor (6) has the following composition:

Stream (H) 29.4% polyarylamine (7.244 kg/h) 4.9% 2,6-dimethylaniline 5.9% hydrogen chloride 59.8% water and is passed in counterflow in multi-stage extractor (7) at 90° C. against an organic phase (stream O) [4.900 kg/h] which is withdrawn as part of distillate stream (E).

The organic phase (M) resulting from extraction stage (7) has the following average composition:
Stream (M) 17.9% polyarylamine
(5.800 kg/h) 81.4% 2,6-dimethylaniline 0.3% hydrogen chloride 0.4% water Stream (M) is taken to process stage (6) as a contribution to the production of stream (B).

The aqueous phase (stream N) resulting from process stage (7) has the following average composition:
Stream (N) 17.2% polyarylamine
(6.344 kg/h) 8.4% 2,6-dimethylaniline 6.5% hydrogen chloride 67.9% water 1.500 kg/h of 2,6-dimethylaniline is added to stream (N) and the stream is then neutralized in neutralization stage (8) with excess aqueous caustic soda solution from tank (3) (major portion of stream Z). The aqueous, salt-containing phase is separated and collected in waste water tank (15).

The organic phase is then washed free of salt in washing stage (9) using water from tank (2). The wash water is also collected in waste water tank (15).

The salt-free washed organic phase (stream J) is separated in distillation stage (12) into a distillation fraction (K) which consists essentially of 2,6-dimethylaniline and a distillation residue (L).

Stream (K) (2.031 kg/h) is combined with the remainder (E') (2.120 kg/h) of stream (E). A portion (2.651 kg/h) is withdrawn from the combined stream and taken to stage (6A). The remainder is added to stream (N) before neutralization stage (8).

The distillation residue from (12) forms, at an average rate of 1.09 kg/h, the second polyamine fraction (L) and is collected in tank (14).

| Polyarylamine GC: | A [wt. %] | G [wt. %] | L [wt. %] |
|---|---|---|---|
| 2,2'-diamino-diphenylmethane | 0.60 | 1.40 | — |
| 2,4'-diamino-diphenylmethane | 13.40 | 31.20 | 0.20 |
| 4,4'-diamino-diphenylmethane | 51.10 | 10.60 | 81.20 |
| N-methyl-4,4'-diaminodiphenyl-methane | 0.50 | 1.20 | <0.10 |
| Σ-diamino-diphenylmethanes | 65.60 | 44.90 | 81.50 |
| Σ-polynuclear-polyamines | 34.40 | 56.10 | 18.10 |
| Partition by amount | 100% | 42.63% | 57.37% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the fractionation and purification of aromatic polyamine mixtures comprising:
    a) mixing the polyamine starting mixture in a first extraction stage with a two-phase system comprising
        (i) a hydrophobic solvent phase which consists essentially of an aromatic auxiliary amine which is slightly soluble in water and exhibits at normal pressure a boiling point which is at least 20° C. below the boiling point of the lowest-boiling component of the starting mixture, and optionally polyamine, and
        (ii) an aqueous phase consisting essentially of water, a strong acid and optionally an auxiliary amine present at least in part in the salt form, and optionally polyamines present at least in part in the salt form, with said first extraction stage operating on the countercurrent principle, and wherein said polyamine starting mixture is introduced into said first extraction stage with said hydrophobic solvent phase, with the proviso that the sum of amine equivalents introduced via polyamine mixture, hydrophobic solvent phase and aqueous phase always exceeds the number of acid equivalents introduced via aqueous phase, and with the further proviso that a first aqueous phase and a first organic phase exit said first extraction stage,
    b) distilling said first organic phase in first distillation stage into
        i) a first fraction consisting essentially of auxiliary amine, and
        ii) a distillation residue consisting essentially of a first polyamine fraction,
    c) neutralizing said first aqueous phase by adding a base thereto and phase separating the resultant mixture into
        i) a second aqueous phase containing the acid in the form of its neutral salt, and
        ii) a second organic phase consisting essentially of polyamine and auxiliary amine, and
    d) separating said second organic phase in a second distillation stage into
        i) a distillate consisting essentially of auxiliary amine, and
        ii) a distillation residue consisting essentially of a second polyamine fraction.

2. A process for fractionating aromatic polyamine mixtures wherein
    a) the initial polyamine mixture (A) is partitioned in a two-phase system consisting of (i) a hydrophobic solvent phase (B) which essentially consists of aromatic auxiliary amine, which is slightly soluble in water and has a boiling point at atmospheric pressure at least 20° C. below the boiling point of the component with the lowest boiling point in the initial mixture, and optionally polyamines, and (ii) an aqueous phase (C) essentially consisting of an aqueous solution of a strong acid and optionally an auxiliary amine which is at least partly in the salt form, and/or optionally polyamines which are at least partly in the salt form using an extraction stage (6) operating on the counterflow principle with thorough mixing of the phases, by introducing the initial polyamine mixture to extraction stage (6) with the hydrophobic solvent phase (B), with the proviso that the amine equivalents introduced to this two-phase system in streams (A), (B) and (C) always exceeds the number of acid equivalents introduced in stream (C), and the organic phase (D) leaving this extraction stage is at least partly separated, after passage through a washing stage and/or neutralization stage (10), in an optionally multi-stage distillation stage (11), into a distillation fraction essentially consisting of auxiliary amine and a first polyamine fraction produced as distillation residue (G), and aqueous phase (H) leaving the first extraction stage (6)
    b) passes, optionally at least partly via an upstream extraction stage (7)
    c) into a neutralization stage (8), the acid contained in the aqueous phase being neutralized with bases, preferably aqueous caustic soda solution and is then mechanically separated in a phase separation step into an aqueous phase containing the acid in the form of its neutral salts and an organic phase containing essentially polyamine and auxiliary amine and d) the organic phase (J) produced in neutralization stage (8), optionally after passage through a washing stage (9), is worked up at least partly in an optionally multi-stage distillation stage (12) into a distillation fraction (K) essentially consisting of auxiliary amine and a second polyamine fraction produced as distillation residue (L).

3. The process of claim 2, wherein b) the aqueous phase (H) produced in extraction stage (6) is at least partly extracted in an upstream extraction stage (7) operated on the counterflow principle, using an organic phase (O) as extraction agent, consisting of auxiliary amine and optionally polyamine, the latter preferably having the composition of the second subproduct (L) and preferably introduced as one constituent of stream (J), the organic phase (M) resulting from process stage (7) being added to stream (B) and thus taken to extraction stage (6) and the aqueous phase (N) resulting from (7) being taken to neutralization stage (8).

4. The process of claim 2, wherein a substream (D") is separated from organic phase (D) leaving extraction stage (6) and is extracted in an optionally multi-stage extraction stage (5), whose first stage is preferably operated as a mixer-settler unit, in counterflow with at least some of, preferably with the entire amount of, stream (X) of aqueous acid and the size of substream (D") is selected so that as extensive a transfer as possible of polyamine contained in (D") to aqueous phase (Q) leaving extraction stage (5) takes place, part of or all of the said aqueous phase (Q) being taken to extraction stage (6) directly and/or via mixer (6A), optionally after the addition of water from stream (Y) and/or auxiliary amine and/or further aqueous acid, as aqueous phase (C), the organic phase (P) produced in (5), essentially consisting of auxiliary amine, likewise being added to organic phase (B) being supplied to extraction stage (6) and used as solvent for the initial polyamine (A).

5. The process of claim 2, wherein aniline or anilines substituted at the nitrogen atom, or anilines substituted in the aromatic ring, are used as auxiliary amine.

6. The process of claim 2, wherein 2,6-dimethylaniline is used as auxiliary amine.

7. The process of claim 2, wherein 2-methyl-6-ethylaniline is used as auxiliary amine.

8. The process of claim 2, wherein N,N-dimethylaniline is used as auxiliary amine.

9. The process of claim 2, wherein mixtures consisting of aniline and/or N-alkyl substituted anilines and/or anilines substituted in the aromatic ring, are used as auxiliary amine.

10. The process of claim 2, wherein xylidine mixtures are used as auxiliary amine.

11. The process of claim 2, wherein technical grade alkylation mixtures of aniline and its derivatives are used as auxiliary amine.

12. The process of claim 2, wherein said polyamine is produced by acid-catalyses aniline/formaldehyde condensation.

13. In a process for the preparation of aromatic polyisocyanates by the phosgenation of aromatic polyamines, the improvement wherein the aromatic polyamine is produced according to the process of claim 1.

14. In a process for the preparation of cycloaliphatic polyamines by the hydrogenation of aromatic polyamines, the improvement wherein the aromatic polyamine is produced according to the process of claim 1.

* * * * *